United States Patent [19]

Asai et al.

[11] 4,335,209
[45] Jun. 15, 1982

[54] PROCESS FOR PREPARATION OF L-TRYPTOPHAN BY ENZYME

[75] Inventors: Yoshiyuki Asai, Yokohama; Masao Shimada, Yamato; Kenji Soda, Uji, all of Japan

[73] Assignee: Mitsui Toatsu Chemicals, Inc., Tokyo, Japan

[21] Appl. No.: 145,267

[22] Filed: Apr. 25, 1980

[30] Foreign Application Priority Data

| May 9, 1979 | [JP] | Japan | 54-55645 |
| Jun. 26, 1979 | [JP] | Japan | 54-79619 |
| Mar. 24, 1980 | [JP] | Japan | 55-36197 |

[51] Int. Cl.³ .................................................. C12P 13/22
[52] U.S. Cl. ................................. 435/108; 435/233; 435/280
[58] Field of Search ................... 435/108, 233, 42, 280

[56] References Cited

U.S. PATENT DOCUMENTS 3,929,573  12/1975  Konosuke et al. ................... 435/108

OTHER PUBLICATIONS

Soda et al., Biochemical and Biophysical Research Communications vol. 35 No. 3 pp. 363-368 (1969).
Osumi, doctoral thesis "Studies on Amino Acid Racemase of Pseudomonas Striata" Kyoto University 1973 (74 pages).
Marconi et al., Agr. Biol. Chem. 38(7), 1343-1349 (1974).
Soda et al., Agr. Biol. Chem. 31(9), 1097-1099 (1967).
Soda et al., Agr. Biol. Chem. 33(3), 424-429 (1969).
Osumi et al., Agr. Biol. Chem. 33(3) 430-435 (1969).

*Primary Examiner*—Lionel M. Shapiro
*Attorney, Agent, or Firm*—Browdy and Neimark

[57] ABSTRACT

A process for the preparation of L-tryptophan comprises reacting indole with serine in the presence of tryptophan synthetase or tryptophanase, wherein DL-serine or D-serine is used and a serine racemizing enzyme is included in the reaction system and reacted with the serine.

10 Claims, No Drawings

PROCESS FOR PREPARATION OF L-TRYPTOPHAN BY ENZYME

BACKGROUND OF THE INVENTION (1) Field of the Invention

The present invention relates to an improvement in the process for the enzymatic preparation of L-tryptophan from indole and serine. More particularly, the present invention relates to an improvement in the process for preparing L-tryptophan by reacting indole with serine in the presence of tryptophan synthetase or tryptophanase.

(2) Description of the Prior Art

For preparing L-tryptophan by utilizing enzymes, there are known several excellent processes in which tryptophan is prepared from indole and serine by utilizing the action of tryptophan synthetase or tryptophanase. For example, the process for preparing L-tryptophan by utilizing the action of tryptophan synthetase is disclosed in "The Journal of Biological Chemistry", 249, pages 7756–7763 (1974), and the process for preparing L-tryptophan by utilizing a tryptophanase-producing microorganism is disclosed in "Vitaminologica et Enzymologica", 29, pages 248–251 (1975).

Indole that is used as one of the starting materials in these known processes is industrially manufactured at a relatively low cost. As the process for the preparation of serine, the other starting material, there are known a protein extracting process, a fermentation process, an enzymatic process and an organic synthesis process. At the present, serine is provided at a lowest cost according to the organic synthesis process. However, the organic synthesis process is defective in that serine prepared according to the organic synthetic process is DL-serine. Only L-serine is capable of being acted on by tryptophan synthetase or tryptophanase and D-serine does not receive the actions of these enzymes at all. Accordingly, the use of DL-serine as the starting material involves an industrial problem.

As the enzymatic process for the synthesis of tryptophan from indole and serine where DL-serine is used as the starting material, there is known a process disclosed in "Agricultural and Biological Chemistry", 38, No. 7, pages 1343–1349 (1974). According to this process, indole and L-serine are converted to L-tryptophan, unreacted D-serine is separated and recovered from the reaction product, D-serine is treated at a high temperature under a high pressure in an aqueous solution to effect racemization, and the racemization product is used as the substrate for the enzymatic reaction. This racemization is accomplished, for example, by treating D-serine under a high pressure at a high temperature such as 160° C. for about 4 hours. By repeating the enzymatic reaction and racemization alternately, DL-series can finally be converted to L-tryptophan substantially completely. This process, however, has various defects as described below.

(1) The condition of racemization is much more violent than that of enzymatic reaction, and therefore, it is impossible to advance both the reactions simultaneously.

(2) If L-tryptophan is present at racemization, not only serine but also L-tryptophan is racemized, and therefore, racemization should be carried out only after complete separation of L-tryptophan to prevent racemization of the latter.

(3) Since the enzyme is deactivated under the racemization conditions, in order to use the enzyme continuously, it is necessary to separate and recover the enzyme before racemization.

(4) A by-product is formed by the racemization heat treatment under pressure which causes coloration of the product, and therefore, purification should be carried out after the reaction.

(5) A large quantity of energy is consumed to carry out the racemization heat treatment under high pressure, and furthermore, after racemization, the liquid reaction mixture should be cooled to the enzymatic reaction temperature.

As will be apparent from the foregoing illustration, the use of DL-serine obtained according to the organic synthesis process, as the starting material for the enzymatic reaction, involves an inherent serious problem, and it will readily be understood that if this problem is effectively solved, synthesis of L-tryptophan will be accomplished very advantageously.

SUMMARY OF THE INVENTION

It is therefore a primary object of the present invention to provide a process for preparing L-tryptophan by reacting indole with L-serine in the presence of tryptophan synthetase or tryptophanase, in which DL-serine or D-serine can be effectively utilized for the preparation of L-tryptophan.

Another object of the present invention is to provide a process in which D-serine can be converted to L-serine without performing a high-temperature high-pressure treatment and in which D-serine can be used as the starting material for the synthesis of L-tryptophan.

Still another object of the present invention is to provide an advantageous process in which DL-serine or D-serine can be converted to L-tryptophan while conducting racemization, without adopting the sequential steps of racemizing DL-serine or D-serine and converting formed L-serine to L-tryptophan.

A further object of the present invention is to provide an economical process for the preparation of L-tryptophan in which the quality of the product can be highly improved and the reaction for the synthesis of L-tryptophan can be accomplished while controlling decomposition of serine.

In accordance with the present invention, the foregoing first and second objects can be attained by a process for the preparation of L-tryptophan which comprises reacting indole with L-serine in the presence of tryptophan synthetase or tryptophanase, wherein indole and DL-serine or D-serine are used and a serine-racemizing enzyme is included in the reaction system to convert at least a part of D-serine to L-serine.

If a serine-racemizing enzyme is made co-present with tryptophan synthetase or tryptophanase in the above-mentioned process and at least a part of D-serine is converted to DL-serine, the above-mentioned third object can be attained.

If tryptophan synthetase or tryptophanase and/or a serine-racemizing enzyme is fixed in the above-mentioned process and ammonium ions are made present in the reaction system, the quality of obtained L-tryptophan can be highly improved and L-tryptophan can be prepared economically advantageously while controlling decomposition of serine.

DETAILED DESCRIPTION OF THE PREFERRED EMBODIMENTS

The "serine racemizing enzyme" that is used in the present invention will be referred to as "serine racemase" hereinafter. As the serine racemase-producing microorganism, the followings can be mentioned, for example, *Pseudomonas putida* IFO 12996, *Brevibacterium leucinophagum* MT-10072, *Pseudomonas desmolytica* MT-10170, *Pseudomonas fragi* MT-10173 and *Pseudomonas taetorolens* MT-10186.

Among these serine racemase producing microorganisms, *Pseudomonas putida* IFO 12996 is a strain which was first identified as *Pseudomonas striata*. Properties of this strain, procedures of extraction of the racemase from cultured cells of this strain and properties of the extracted racemase are disclosed in "Agricultural and Biological Chemistry", 31, No. 9, pages 1097–1099 (1967), ibid, 33, No. 3, pages 424–429 (1969), ibid, 33, No. 3 pages 430–435 (1969), "Biochemical and Biophysical Research Communications", 35, No. 3, pages 363–368 (1969), and the thesis for a doctor's degree entitled "Studies on Amino Acid of Racemase of *Pseudomonas Siriata*", submitted by Mr. Takaharu Osumi at Kyoto University, Agricultural Department (Japan). The above Japanese report teaches that this racemase is called "low substrate specificity amino acid racemase" and that 20 kinds of amino acids including lysine, $\epsilon$-N-acetyl-lysine and serine can be substrates for this racemase and 13 kinds of amino acids including $\alpha$-N-acetyl-lysine cannot be substrates for this racemase. It also is indicated that when serine is a substrate for this racemase, the relative activity of serine is 8.7 and is much lower than that (100) of lysine or $\epsilon$-N-acetyl-lysine. However, behaviors of this racemase to tryptophan have not been disclosed.

Research has now been conducted on the properties of this low substrate specificity racemase, and it has been found that this racemase does not racemize tryptophan, it does not receive enzymatic inhibition by L-tryptophan, it exerts an effective activity under optimum reaction temperature and pH conditions for preparing L-tryptophan from indole and L-serine in the presence of tryptophan synthetase or tryptophanase, and it has properties suitable for the synthesis of L-tryptophan. Based on this finding, microorganisms capable of producing serine racemase have been researched and the above-mentioned strains have been found.

Extraction of the low substrate specificity amino acid racemase from *Pseudomonas putida* IFO 12996, one of serine racemase producing strains, is accomplished, for example, by the process comprising the following 6 steps: (1) crude extraction, (2) ammonium sulfate precipitation, (3) first chromatography using diethylaminoethyl cellulose, (4) second chromatography using diethylaminoethyl cellulose, (5) chromatography using Sephadex G-200 (tradename for the product of Pharmacia Fine Chemicals Co.) and (6) crystallization. The extraction and purification process is described in detail in "Biochemical and Biophysical Research Communications", 35, No. 3, pages 363–368 (1969).

As the strain producing tryptophan synthetase that is used in the present invention, there can be mentioned, for example, *Escherichia coli* MT-10231, *Escherichia coli* MT-10232, *Escherichia coli* MT-10238 and *Neurospora crassa* ATCC 14692. The process for extracting tryptophan synthetase from cultured cells of *Escherichia coli* is described in "The Journal of Biochemistry", 252, No. 19, pages 6594–6599 (1977), and the process for extracting tryptophan synthetase from cultured cells of *Neurospora crassa* is described in "The Journal of Biological Chemistry", 250, 8, pages 2941–2946 (1975).

As the strain capable of producing tryptophanase that is used in the present invention, there can be mentioned, for example, *Proteus vulgaris* IFO 3167, *Escherichia coli* IAM 1268, *Aerobacter aerogenes* IFO 12019, *Klebsiella pneumoniae* ATCC 8724 and *Bacillus alvei* ATCC 6348. The process for extracting tryptophanase from cultured cells is described in "Amino Acid and Nucleic Acid", No. 31, pages 102–112 (1975). Tryptophanase commercially available as a reagent can be used in the present invention.

Any of synthetic and natural culture media may be used for culturing strains producing tryptophan synthetase, tryptophanase or serine racemase, so far as it contains a carbon source, a nitrogen source, an inorganic substance and, if necessary, a small amount of a nutrient. In culturing the tryptophan synthetase producing strain, it is ordinarily necessary to add a minute amount of tryptophan, anthranilic acid or indole to a culture medium. In culturing the tryptophanase producing strain, since tryptophanase is an inducing enzyme, if tryptophan is added in an amount of about 0.1 to about 0.5% by weight to a culture medium, cultured cells having a high tryptophanase activity can be obtained. Any of carbon sources and nitrogen sources that can be utilized by the strain used can be used. For example, as the carbon source, there can be used carbohydrates such as glucose, glycerol, fructose, sucrose, maltose, mannose, starch, hydrolyzed starch and molasses. As the nitrogen source, there can be used, for example, various organic and inorganic ammonium salts such as ammonia, ammonium chloride, ammonium sulfate, ammonium carbonate and ammonium acetate, and natural organic nitrogen sources such as meat extract, yeast extract, corn steep liquor, hydrolyzed casein, fish meal, digested fish meal, defatted soybean and digested defatted soybean. Most of natural organic nitrogen sources can act not only as the nitrogen source but also as the carbon source. When inorganic substances such as potassium dihydrogen phosphate, dipotassium hydrogen phosphate, potassium chloride, sodium chloride, magnesium sulfate and ferrous sulfate are used according to need, good results can be obtained.

Culturing is carried out under aerobic conditions according to the shaking culturing method or aerated agitating submerged culturing method. The culturing temperature is in the range of from 20° to 50° C. It is preferred that the pH of the culture medium be maintained at a neutral or weakly alkaline level during culturing. Ordinarily, the culturing period is 1 to 7 days.

Each of tryptophan synthetase, tryptophanase and serine racemase obtained by conducting the culturing according to the above-mentioned procedures may be used in the form of living cells collected from the culturing medium of the enzyme producing strain, dried cells, treated cells obtained by subjecting cells to a pulverization, autolysis or sonic treatment, extracts from these cells, a crude enzyme obtained from such extracts or a pure enzyme. In the present invention, the above-mentioned enzymes may be used after they have been fixed according to known methods customarily adopted for fixing enzymes, for example, the carrier bonding method, the crosslinking method and the including method. In the carrier bonding method, the enzyme is bonded to a carrier such as a natural polymer, its derivative, a synthetic polymer or an inorganic substance according to the covalent bonding method such as the diazo method, peptide method, alkylation method or acylation method, the ion bonding method, the physical adsorption method, the biological adsorption method or the adsorption method utilizing the biochemical affinity. In the cross-linking method, the enzyme is fixed by using a bifunctional reagent. As the including method, there can be adopted the so called lattice method in which a molecule of the living enzyme is included in a gel formed by polymerization of acrylamide or the like, and the so-called microcapsule method in which the enzyme is confined in a microcapsule of a semi-permeable membrane of a natural polymer or synthetic polymer.

In the process of the present invention, these enzyme fixing methods are appropriately chosen and adopted according to various reaction modes described hereinafter. In general, however, the including method using an acrylamide type monomer is frequently used as the preferred method. As the acrylamide type monomer, there can be used, for example, acrylamide, N-N'-methylene-bis-acrylamide and diacrylamide methyl ether. Polymerization of such monomer is carried out in the presence of a polymerization initiator such as potassium persulfate, ammonium persulfate, vitamin $B_1$ or Methylene Blue and a polymerization promotor such as $\beta$-(dimethylamino)-propionitrile or N,N,N',N'-tetramethyl-ethylene diamine.

If tryptophan synthetase or tryptophanase and/or serine racemase is fixed according to the above-mentioned fixing method and used in the fixed state for the reaction, preparation of L-tryptophan can be advantageously accomplished. More specifically, L-tryptophan formed by the enzymatic process inevitably contains impurities such as cells, materials used for culturing and various proteins and L-tryptophan having a high purity can hardly be obtained, and since it is relatively difficult to separate the enzyme from L-tryptophan, it is difficult to use the enzyme repeatedly. In contrast, if the fixed enzyme is used, elution of impurities derived from the enzyme into the aqueous solution of formed L-tryptophan is remarkably controlled and therefore, the purity of obtained L-tryptophan can be remarkably improved. Furthermore, it is possible to use the enzyme repeatedly and the freedom of the process for the preparation of L-tryptophane can be prominently increased.

As specific means for converting at least a part of D-serine to L-serine by the action of the serine racemase and preparing L-tryptophan in the process of the present invention where indole and DL-serine or D-serine are used as the starting materials, there are adopted the reaction of converting L-serine to L-tryptophan by the action of tryptophan synthetase or tryptophanase and the reaction of racemizing serine by the action of the serine racemase. The two reactions may be simultaneously carried out in one reaction vessel or they may be carried out independently in different reaction vessels. However, the process in which the serine racemase is made copresent with tryptophan synthetase or tryptophanase and L-tryptophan is prepared by one step is advantageous from the economical viewpoint and the reaction procedures can be simplified in this process. When DL-serine is used and this process is adopted, since L-serine is converted to L-tryptophan and simultneously, D-serine is sequentially racemized to DL-serine and converted to L-tryptophan, it is possible to convert the starting DL-serine to L-tryptophan in a high yield by simple equipments. Also when D-serine is used, since conversion to L-tryptophan is advanced simultaneously with the racemizing reaction, the conversion is accomplished substantially in the same manner in as in the case where DL-serine is used.

As described hereinbefore, in the process of the present invention, the reaction of conversion to L-tryptophan and the reaction of recemization of serine may be carried out independently or simultaneously. When the enzyme is used in the fixed state, appropriate fixing methods may be selected according to the above-mentioned reaction modes. More specifically, in the process of the present invention, there may be adopted a method in which only tryptophane synthetase or tryptophanase is fixed and a method in which tryptophan synthetase or tryptophanase and serine racemase are fixed, and these two methods may be combined with the above-mentioned method in which both the enzymes are caused to act separately or simultaneously. Furthermore, there may be adopted a method in which both the fixed enzymes are used in combination or separately, a batch method and a continuous method using a column or the like.

The enzyme concentrations, the amounts of substrates such as indole, DL-serine and D-serine and the amounts of enzymes fixed on carriers may be appropriately changed according to the above-mentioned reaction modes.

The amounts of substrates such as indole, DL-serine and D-serine in the reaction system and the ratio of the amount of indole to the amounts of DL-serine and D-serine are not particularly critical in the present invention, but the substrate concentration in the liquid is ordinarily 0.01 to 20% by weight and the above-mentioned amount ratio of the substrates may optionally be chosen. However, it is ordinarily preferred that the concentration of indole dissolved in the reaction liquid be lower than 500 ppm, especially about 100 ppm. Accordingly, when it is desired to accumulate L-tryptophan at a high concentration, there is often adopted a method in which indole is added gradually and continuously so that the concentration of indole is not great at any one time. When this continuous addition method is not adopted, the dissolved indole concentration may be elevated to about 10% by weight by incorporating a surface active agent, for example, Triton X-100 (trademark for the polyoxyethylene alkylphenol ether type non-ionic surface active agent manufactured and sold by Wako Junyaku Kogyo) into the reaction system. The amount added of the surface active agent is preferably 1 to 10% by weight, particularly about 5% by weight, in the aqueous solution, though the amount added of the surface active agent is varied to some extent according to the indole concentration. The solubility of DL-serine in the aqueous solution is about 6% by weight at 30° C., and the solubility of either D-serine or L-serine in the aqueous solution is about 25% by weight at 30° C. However, it may be said that if the serine concentration is up to 10% by weight in the aqueous solution, then the higher the concentration, the higher will be the reaction speed.

The amounts of tryptophan synthetase, tryptophanase and serine racemase present in the reaction system are changed according to the above-mentioned methods of separation, purification and treatment of the enzymes, but they are not particularly critical and they may be appropriately determined depending on the desired amount ratio of the substrates, the activities of the enzymes and other factors. However, if the amount of serine racemase is much smaller than the amount of tryptophan synthetase or tryptophanase, the amount of L-serine in the reaction liquid is small and the reaction speed is low. On the other hand, if the amount of tryptophan synthetase or tryptophanase is much smaller than the of serine racemase, the amount ratio of D-serine to L-serine will be about 1 but the speed of formation of L-tryptophan becomes low. Accordingly, the concentrations of tryptophan synthetase or tryptophanase and the ratio thereof should be appropriately determined according to the L-tryptophan-forming conditions adopted.

In the process of the present invention, it is possible to add fresh substrates with the advance of the reaction. Furthermore, it is possible to withdraw a part or all of formed L-tryptophan from the reaction system with advance of the reaction. In carrying out the reaction of the present invention, pyridoxal phosphate, which is a coenzyme, may be incorporated into the reaction liquid in a minute amount, for example, at a concentration of 1 to 100 ppm in the reaction liquid, in addition to the substrates.

When tryptophan synthetase or tryptophanase is used in the form of enzyme-containing cultured cells of the enzyme-producing microorganism or an extract from such cells, since an enzyme decomposing L-serine and/or D-serine is ordinarily contained in such cells or extract, ammonium ions capable of inhibiting such decomposition are incorporated in the reaction liquid.

Several enzymatic reactions using serine as one reactant are known. However, decomposition of serine in these reaction systems or inhibition of this decomposition is not described in any of literature references. As one reason, there can be mentioned the fact that decomposition is hardly observed in these reactions or is negligible if pure enzymes are used. However, if cultured cells of microorganisms or extracts from such cultured cells are used as enzymes, decomposition of serine cannot be neglected.

Research has now been conducted with a view to developing a method in which decomposition of L-serine and/or D-serine by cultured cells of microorganisms or extracts therefrom is effectively inhibited, and it has been found that if ammonium ions are made present in the reaction liquid, decomposition of serine can be effectively inhibited. The concentration of the ammonium ion present in a serine-containing aqueous solution differs according to the temperature and pH of the aqueous solution and the properties of the enzymes used for the reaction, and it is impossible to define the concentration simply. However, the ammonium ion concentration is ordinarily 0.01 to 2 moles per liter of the aqueous solution and preferably 0.1 to 2 moles per liter of the aqueous solution. A higher ammonium ion concentration is preferred for attaining the object of inhibiting decomposition of serine. However, if the ammonium ion concentration is too high, even the intended reaction is inhibited or separation of the intended reaction product from the reaction liquid becomes very difficult. Accordingly, it is preferred that the ammonium ion concentration be maintained at a low level within a range enabling inhibition of decomposition of serine. Therefore, the upper limit of the ammonium ion concentration is set at 2 moles per liter of the aqueous solution and the ammonium ion concentration is ordinarily adjusted at 0.1 to 0.5 mole per liter of the aqueous solution. This feature that decomposition of serine can be specifically inhibited at such a low ammonium ion concentration is very advantageous from the industrial viewpoint. Any of compounds providing ammonium ions in an aqueous solution can be used as the compound for making ammonium ions present in the reaction system. For example, there can be mentioned various inorganic and organic ammonium salts such as ammonium chloride, ammonium sulfate, ammonium phosphate, ammonium nitrate, ammonium carbonate and ammonium acetate, and ammonia.

The reaction temperature for formation of L-tryptophan by using tryptophan synthetase or tryptophanase and serine racemase is ordinarily 20° to 60° C., and preferably 30° to 45° C. The pH value adopted for the reaction is ordinarily 6.0 to 11.0 and particularly 7.5 to 9.0. These reaction conditions are appropriately adjusted according to the reaction methods adopted, for example, the method in which the substrates are passed through a suspensoid or fixed bed of fixed tryptophan synthetase or tryptophanase and fixed serine racemase, the method in which tryptophan synthetase or tryptophanase and the substrates are passed through a fixed bed of fixed serine racemase and the method in which serine racemase and the substrates are passed through a fixed bed of fixed tryptophan synthetase or tryptophanase.

Isolation of formed L-tryptophan from the reaction liquid can easily be accomplished by an adsorption-desorption treatment using an ion exchange resin, active carbon or the like. More specifically, if L-tryptophan is precipitated in the form of a crystal in the reaction liquid, water is added to dissolve the crystal, the insoluble substances such as cells are removed from the reaction liquid by centrifugal separation or filtration, and L-tryptophan is ordinarily recovered according to any of the following methods: (1) a method in which the pH value of the reaction liquid is adjusted to the isoelectric point to precipitate L-tryptophan and the precipitated L-tryptophan is recovered, (2) a method in which L-tryptophane is adsorbed by using an ion exchange resin and it is then desorbed therefrom, (3) a method in which L-tryptophan is precipitated in the form of a hardly soluble metal salt and the precipitated metal salt is recovered, (4) a method in which a water-soluble organic solvent is added to the filtrate to effect crystallization and the resulting crystal is recovered, and (5) a method in which the filtrate is subjected to electrodialysis and separated L-tryptophan is recovered.

The present invention will now be described in detail with reference to the following Examples that by no means limit the scope of the invention.

In these Examples, the qualitative confirmation of formed L-tryptophan was made based on the Rf value of L-tryptophan on the paper chromatogram, the ultraviolet absorption values and the coloration test using Ehrlich's reagent. The quantitative determination was made based on the absorbance value of the spot extract on the paper chromatogram at 280 mμ and according to the bioassay. In the Examples, all "%" are by weight.

EXAMPLE 1

One platinum loop of *Escherichia coli* MT-10232 was inoculated on 50 ml of a culture medium of a culture medium composition I described below, and shaking culturing was carried out at 30° C. for 20 hours. Culture medium composition I:
Meat extract: 1.0%
Peptone: 0.5%

Yeast extract: 0.1%
KH$_2$PO$_4$: 0.2%
Initial pH: 7.0

Then, 1 l of the culture liquid was subjected to centrifugal separation to collect cells, and the collected cells were used as the enzyme source of tryptophan synthetase.

One platinum loop of *Pseudomonas putida* IFO 12996 was inoculated on 50 ml of a culture medium composition II described below, and 1 l of the culture liquid was subjected to centrifugal separation to collect cells. The collected cells were used as the enzyme source of serine racemase.

Culture medium composition II:
Meat extract: 1.0%
Peptone: 1.0%
NaCl: 0.5%

In 50 g of Triton X-100 was dissolved 20 g of indole, and 36 g of DL-serine, 1 g of Na$_2$SO$_3$, 100 mg of pyridoxal phosphate and the above-mentioned two kinds of cells collected by centrifugal separation were added to the solution so that the entire volume was 1 l. The reaction liquid was shaken at a temperature of 30° C. and pH of 8.5 for 72 hours to effect reaction. After the reaction, 28.5 g of L-tryptophan was formed and accumulated in the reaction liquid (the yield was 41% based on serine).

For comparison, the reaction was carried out in the same manner as described above except that the cultured cells of the serine racemase-producing strain were not added. After the reaction, L-tryptophan was accumulated in an amount of 23.5 g (the yield was 34% based on serine) and the amount accumulated of L-tryptophan was smaller by 5.0 g than in the run where both the enzymes, that is, serine racemase and tryptophan synthetase, were used for the reaction.

EXAMPLE 2

The experiment was carried out in the same manner as described in Example 1 except that *Escherichia coli* MT-10238 was used instead of *Escherichia coli* MT-10231 used in Example 1. It was found that 27.8 g of L-tryptophan was accumulated in the reaction liquid (the yield was 40% based on serine). In a comparative run where serine racemase was not added, accumulation of L-tryptophan was not observed.

EXAMPLE 3

The experiment was carried out in the same manner as described in Example 1 except that *Aerobacter aerogenes* IFO 3317, a tryptophanase-producing strain, was used instead of *Escherichia coli* MT-10231 used in Example 1 and a culture medium of a culture medium composition III described below was used instead of the culture medium of the culture medium composition I. It was found that 22.2 g of L-tryptophan was accumulated in the reaction liquid. In a comparative run where serine racemase was not added, the amount accumulated of L-tryptophan was 19.3 g (the yield was 28% based on serine). Culture medium composition III:
L-Tryptophan: 0.2%
KH$_2$PO$_4$: 0.5%
MgSO$_4$.7H$_2$O: 0.05%
Corn steep liquor: 6.00%
Casamino acid: 2.0%
Initial pH: 8.0

EXAMPLE 4

Cultured cells of the tryptophan synthetase-producing strain and cultured cells of the serine racemase-producing strain, separated according to the method described in Example 1, were separately suspended in pure water to form 100 ml each of the suspensions. Each suspension was mixed with 15 g of acrylamide, 1 g of N,N'-methylene-bis-acrylamide, 15 ml of 4% β-(dimethylamino)-propionitrile and 10 ml of 2% potassium persulfate, and the mixture was allowed to stand still at room temperature for 15 minutes. The reaction product was pulverized and washed with pure water. Thus, 150 g each of the fixed enzymes were obtained.

Then, 150 g each of the fixed enzymes, 1.0 g of indole, 2.0 g of DL-serine, 1 g of sodium sulfate and 100 mg of pyridoxal phosphate were added to water so that the entire volume was 1 l. The reaction liquid was shaken at 30° C. for 72 hours to effect reaction. It was found that 1.14 g of L-tryptophan was accumulated in the reaction liquid after the reaction (the yield was 29% based on serine).

The fixed enzymes were separated from the reaction liquid after the reaction, and formed L-tryptophan was separated from the residual liquid and simultaneously, a substrate solution containing indole, DL-serine and other additives dissolved therein was added to the separated fixed enzymes. The reaction was repeated in the same manner as described above. Even after the fixed enzymes were thus used repeatedly 30 times, the amount formed of L-tryptophan was hardly reduced at all.

Incidentally, separation of the fixed enzymes by filtration was accomplished very easily.

For comparison, the reaction was carried out in the same manner as described above except that the cultred cells of the serine racemase-producing strain were not used. After the reaction, L-tryptophan was accumulated only in an amount of 0.94 g in the reaction liquid (the yield was 24% based on serine).

EXAMPLE 5

The experiment was carried out in the same manner as described in Example 4 except that *Aerobacter aerogenes* IFO 3317, a tryptophanase-producing strain, was used instead of *Escherichia coli* MT-10231 used in Example 4 and the culture medium of the culture medium composition III was used. It was found that 0.89 g of L-tryptophan was accumulated (the yield was 23% based on serine). In a comparative run where serine racemase was not added, the amount accumulated of L-tryptophan was 0.77 g (the yield was 20% based on serine).

REFERENTIAL EXAMPLE 1

*Escherichia coli* W was cultured at 30° C. and pH of 7.2 at an aeration rate of 10 l/min for 21.5 hours in a jar fermentor having a capacity of 20 liters, which was charged with 10 l of a culture medium having a composition described below. As the result, 315 g of cells having a water content of 80% were obtained. Culture medium composition:
Glucose: 2.00%
(NH$_4$)$_2$SO$_4$: 0.50%
KH$_2$PO$_4$: 0.10%
MgSO$_4$: 0.05%
Indole: 0.01%
Casamino acid: 0.025%

Then, 0.16 g of the so collected cells were put into a test tube charged with a reaction liquid having a composition described below and the mixture was shaken at 30° C.

Composition of reaction liquid:
L-Serine: 1.91%
$Na_2SO_3$: 0.10%
Pyridoxal phosphate: 0.01%
$(NH_4)_2SO_4$: 0 to 2.46% (variable)

After the reaction had been conducted for 48 hours, the content of L-serine was analyzed by high speed liquid chromatography to obtain results shown in Table 1.

TABLE 1

|  | Run 1 | Run 2 | Run 3 | Run 4 |
|---|---|---|---|---|
| $(NH_4)_2SO_4$ Concentration (%) | 0 | 0.615 | 1.23 | 2.46 |
| (Ammonium Ion Concentration, mole/l) | (0) | (0.10) | (0.19) | (0.37) |
| L-Serine Concentration (g/l) | 3.8 | 8.5 | 15.4 | 19.1 |
| L-Serine Decomposition Ratio (%) | 79.3 | 55.5 | 19.4 | 0 |

As is seen from the results shown in Table 1, when the ammonium ion concentration was 0 mole/l, the L-serine decomposition ratio was 79.3%, but as the ammonium ion concentration was increased, the L-serine decomposition ratio was decreased and when the ammonium ion concentration was 0.37 mole/l, the L-serine decomposition ratio was reduced to 0%.

REFERENTIAL EXAMPLE 2

The cells obtained in Example 1 were stored at −15° C. for a long time, and 0.32 g of the cells were put in a test tube charged with 10 ml of a reaction liquid having a composition indicated below. The mixture was shaken at 30° C. for 48 hours, and D-serine was analyzed in the same manner as in Referential Example 1.

Composition of reaction liquid:
D-serine: 2.03%
$Na_2SO_3$: 0.10%
Pyridoxal phosphate: 0.01%
$NH_4Cl$: 0–2% (variable)

The obtained results are shown in Table 2.

TABLE 2

|  | Run 1 | Run 2 | Run 3 |
|---|---|---|---|
| $NH_4Cl$ Concentration (%) | 0 | 0.1 | 2.0 |
| (ammonium ion concentration mole/l) | (0) | (0.02) | (0.37) |
| D-Serine Concentration (g/l) | 1.2 | 11.5 | 17.9 |
| D-Serine Decomposition Ratio (%) | 94.0 | 43.3 | 11.8 |

From the results shown in Table 2, it was found that not only L-serine but also D-serine is decomposed and the D-serine decomposition ratio is decreased with increase of the ammonium ion concentration.

REFERENTIAL EXAMPLE 3

*Pseudomonas putida* IFO 12996 was inoculated on 150 ml of a culture medium of a composition described below, which was charged in a Sakaguchi flask having a capacity of 500 ml, and shaking culturing was carried out at 30° C. for 24 hours.

Composition of culture medium:
Meat extract: 0.3%
Polypeptone: 0.5%
Glucose: 3.0%
pH: 7.0

After the culturing, cells were collected by centrifugal separation. By using the so collected cells in an amount corresponding to 20 ml of the culture liquid, the influence of the ammonium ion on the decomposition of serine was examined. The experiment was conducted separately on L-serine and D-serine. The obtained results are shown in Table 3.

TABLE 3

|  | Run 1 | Run 2 | Run 3 |
|---|---|---|---|
| $NH_4Cl$ Concentration (%) | 0 | 0.5 | 2.0 |
| (ammonium ion concentration, mole/l) | (0) | (0.10) | (0.38) |
| L-Serine Concentration[1] (g/l) | 0 | 13.3 | 18.9 |
| L-Serine Decomposition Ratio (%) | 100 | 30.0 | 0 |
| D-Serine Concentration[2] (g/l) | 3.8 | 8.7 | 17.5 |
| D-Serine Decomposition Ratio (%) | 81.3 | 57.1 | 13.8 |

Note
[1] The initial L-serine concentration was 19.0 g/l.
[2] The initial D-serine concentration was 20.3 g/l.

EXAMPLE 6

In 1 l of a reaction liquid having a composition described below, 31.5 g of the wet cells obtained in Referential Example 1 were incorporated, and reaction was carried out at 35° C. for 10 hours. Formed L-tryptophan and L-serine were analyzed according to high speed liquid chromatography.

Composition of reaction liquid:
Indole: 2.0%
L-Serine: 3.0%
$Na_2SO_3$: 0.10%
Pyridoxal phosphate: 0.01%
$(NH_4)_2SO_4$: 0 or 2.5%
(ammonium ion concentration): (0 or 0.19 mole/l)

The indole was gradually added over a period of 10 hours while the reaction was conducted.

After the reaction had been conducted for 10 hours, the amounts of L-tryptophan and L-serine in the reaction liquid were determined to obtain results shown in Table 4.

TABLE 4

|  | Formed L-Tryptophan (%) | Residual L-Serine (%) |
|---|---|---|
| $(NH_4)_2SO_4$ not added | 2.51 | below 0.1 |
| 2.5% $(NH_4)_2SO_4$ added | 3.49 | 1.18 |

From the results shown in Table 4, it is seen that when 2.5% of $(NH_4)_2SO_4$ was added, L-tryptophan was formed in a yield of 100% based on added indole and residual L-serine was hardly decomposed, while if ammonium sulfate was not added, the yield of L-tryptophan was low and residual L-serine was substantially decomposed.

What we claim is:

1. A process for the enzymatic preparation of L-tryptophan which comprises reacting indole with L-serine in the presence of tryptophan synthetase or tryptophanase, wherein DL-serine or D-serine is used as the starting material and DL-serine or D-serine is reacted with serine racemase which does not racemize tryptophan to convert at least a part of D-serine to L-serine, said serine racemase being present with tryptophan synthetase or trytophanase to simultaneously react L-serine with indole.

2. A process according to claim 1, wherein the reaction is carried out at a temperature of 20° to 60° C. and pH of 6.0 to 11.0.

3. A process according to claim 1, wherein the reaction is carried out at a temperature of 30° to 45° C. and pH of 7.5 to 9.0.

4. A process according to claim 1, wherein tryptophan synthetase or tryptophanase, or serine racemase is fixed.

5. A process according to claim 1, wherein tryptophan synthetase or tryptophanase and serine racemase are fixed.

6. A process according to claim 1, wherein cultured cells of a microorganism containing tryptophan synthetase or tryptophanase or serine racemase or extracts thereof are used.

7. A process according to claim 6, wherein ammonium ion is present in the reaction liquid in an amount of 0.01 to 2 moles/l.

8. A process according to claim 6, wherein ammonium ion is present in the reaction liquid in an amount of 0.1 to 0.5 mole/l.

9. A process according to claim 7 wherein the ammonium ion is an inorganic or organic ammonium ion.

10. A process for the enzymatic preparation of L-tryptophan which comprises reacting indole with L-serine in the presence of tryptophane synthetase or tryptophanase wherein DL-serine or D-serine is used as the starting material and DL-serine or D-serine is reacted with serine racemase to convert at least a part of D-serine to L-serine, said serine racemase being present in the form of cultured cells of a microorganism containing serine racemase or extracts thereof, the reaction medium further containing ammonium ion present in an amount of 0.01 to 2 mols per liter.

* * * * *